US011234918B2

(12) United States Patent
Milow et al.

(10) Patent No.: US 11,234,918 B2
(45) Date of Patent: Feb. 1, 2022

(54) METHODS FOR BOTANICAL AND/OR ALGAE EXTRACTION

(71) Applicants: BASF CORPORATION, Florham Park, NJ (US); BASF BEAUTY CARE SOLUTIONS FRANCE SAS, Lyons (FR); Clifford A. Milow, Massapequa, NY (US); Laurent Bailly, Essey les Nancy (FR); Christopher Judd, Riverhead, NY (US); Nicole Jeannine Richter, Port Jefferson, NY (US)

(72) Inventors: Clifford A. Milow, Massapequa, NY (US); Laurent Bailly, Essey les Nancy (FR); Christopher Judd, Riverhead, NY (US); Nicole Jeannine Richter, Port Jefferson, NY (US)

(73) Assignee: BASF CORPORATION, Florham Park, NJ (US)

( * ) Notice: Subject to any disclaimer, the term of this patent is extended or adjusted under 35 U.S.C. 154(b) by 1423 days.

(21) Appl. No.: 14/402,719

(22) PCT Filed: Jun. 6, 2013

(86) PCT No.: PCT/US2013/044464
§ 371 (c)(1),
(2) Date: Nov. 21, 2014

(87) PCT Pub. No.: WO2013/184884
PCT Pub. Date: Dec. 12, 2013

(65) Prior Publication Data
US 2015/0140141 A1 May 21, 2015

Related U.S. Application Data

(60) Provisional application No. 61/656,221, filed on Jun. 6, 2012.

(51) Int. Cl.
A61K 8/49 (2006.01)
A61Q 1/06 (2006.01)
A61Q 19/00 (2006.01)
A61Q 19/10 (2006.01)
A61K 8/86 (2006.01)
A61K 8/60 (2006.01)
A61K 36/06 (2006.01)
A61K 36/02 (2006.01)
A61K 36/18 (2006.01)
A61K 8/9706 (2017.01)
A61K 8/9728 (2017.01)
A61K 8/9789 (2017.01)
A61Q 19/08 (2006.01)
A61Q 1/14 (2006.01)
A61Q 17/04 (2006.01)

(52) U.S. Cl.
CPC .............. *A61K 8/498* (2013.01); *A61K 8/604* (2013.01); *A61K 8/86* (2013.01); *A61K 8/9706* (2017.08); *A61K 8/9728* (2017.08); *A61K 8/9789* (2017.08); *A61K 36/02* (2013.01); *A61K 36/06* (2013.01); *A61K 36/18* (2013.01); *A61Q 1/06* (2013.01); *A61Q 19/00* (2013.01); *A61Q 19/004* (2013.01); *A61Q 19/10* (2013.01); *A61K 2236/00* (2013.01); *A61K 2800/10* (2013.01); *A61Q 1/14* (2013.01); *A61Q 17/04* (2013.01); *A61Q 19/005* (2013.01); *A61Q 19/08* (2013.01)

(58) Field of Classification Search
CPC ............ A61K 2236/00; A61K 2800/10; A61K 36/02; A61K 36/06; A61K 36/18; A61K 8/498; A61K 8/604; A61K 8/86; A61K 8/97; A61K 8/9706; A61K 8/9728; A61K 8/975; A61K 8/9789; A61K 8/99; A61Q 17/04; A61Q 19/00; A61Q 19/004; A61Q 19/005; A61Q 19/08; A61Q 19/10; A61Q 1/06; A61Q 1/14; A61P 17/00
See application file for complete search history.

(56) References Cited

U.S. PATENT DOCUMENTS

| 6,471,973 B1 | 10/2002 | Perriu et al. |
| 6,485,756 B1 | 11/2002 | Aust et al. |
| 8,828,142 B2 | 9/2014 | Oliviera et al. |
| 2004/0101508 A1* | 5/2004 | Pauly .................. A61K 8/97 424/74 |
| 2005/0148088 A1 | 7/2005 | Ong |

(Continued)

FOREIGN PATENT DOCUMENTS

| CN | 1436572 | 8/2003 |
| KR | 100741644 | 7/2007 |

(Continued)

OTHER PUBLICATIONS

Glatter et al., Characterization of a Poly(ethylene oxide)-Poly(propylene oxide) Triblock Copolymer (EO27-PO39-EO27) in SAqueous solution, 1994, Macromolecules, 27:6046-6054.*
International Search Report dated Oct. 29, 2013.
Abstract 440—Extraction and Recovery of Fermentation Products using Block Copolymer Surfactants, Bernice Perez, et al.

(Continued)

*Primary Examiner* — Aaron J Kosar
(74) *Attorney, Agent, or Firm* — Lowenstein Sandler LLP

(57) ABSTRACT

The present disclosure relates to methods for extraction of biomass. Biomass of most interest is that which contains biologically active, extracts suitable for the skin care market. The biomass of interest includes botanicals (plant extracts and bioferments thereof), algae (red, brown, green and red, including bioferments thereof), fungi and even animal extracts (insect, crustacean) origin. Further the use of said extracts in cosmetic preparations prepared by the disclosed method is envisioned.

7 Claims, 2 Drawing Sheets

(56) References Cited

U.S. PATENT DOCUMENTS

| | | |
|---|---|---|
| 2006/0078633 A1 | 4/2006 | Na et al. |
| 2006/0099690 A1 | 5/2006 | Chang et al. |
| 2010/0047219 A1 | 2/2010 | Ceccoli et al. |
| 2011/0190175 A1 | 8/2011 | Steinbrenner et al. |
| 2012/0011589 A1 | 1/2012 | Kanaya et al. |
| 2013/0010390 A1 | 1/2013 | Watanabe et al. |
| 2013/0225586 A1 | 8/2013 | Kanaya et al. |

FOREIGN PATENT DOCUMENTS

| | | |
|---|---|---|
| WO | 03095979 | 11/2003 |
| WO | 20090124370 | 10/2009 |

OTHER PUBLICATIONS

AIChE Journal, Sep. 1994, vol. 40, No. 9—Separations—Extraction of Naphthalene by Block Copolymer Surfactants Immobilized in Polymeric Hydrogels, p. 1449-1458.

China Particuology, Chen Guo, et al., vol. 3, No. 6, 2005, p. 310-316—Advances in Microemultion Phase on Self-Assembly and Micelle Extraction with Block Copolymers.

Critical Reviews in Analytical Chemistry, Willie L. Hinze, vol. 24, No. 2, 1993, p. 133-177—A Critical Review of Surfactant-Mediated Phase Separations.

Ind. Eng. Chern. Res. 1996, Paul J.M. Lebens, et al., vol. 35, p. 3415-3421—Temperature-Induced Solubilization of Hydrocarbons in Aqueous Block Copolymer Solutions.

Journal of Chemical Technology and Biotechnology, Francislene A. Hasmann, et al., vol. 83, 2008, p. 167-173—Aqueous two-phase Extraction using Thermospearating Copolymer: a New System for Phenolic Compounds Removal from Hemicelullosic Hydrolysate.

Journal of Chromatography A, 718 (1995), p. 67-79—Effects of Salts and the Surface Hydrophobicity of Proteins on Partitioning in Aqueous Two-phase Systems Containing Thermoseparating Ethylene Oxide-Propylene Oxide Copolymers.

Langmuir 1992, 8, p. 1291-1299, Patricia N. Hurter, et al.—Solubilization of Polycyclic Aromatic Hydrocarbons by Poly (ethylene oxide-propylene oxide) Block Copolymer Micelles: Effects of Polymer Structure.

Phytochemical Analysis, 19, 2008 p. 160-163, Chen Sun, et al.—Analysis of Glycyrrhizic Acid and Liquiritin in Liquorice Yoot with Microwave-assisted Micellar Extraction and Pre-concentration.

Romanian Academy, Organic Chemistry Center, Vasile Dinoiu, et al. vol. 62, No. 4, 2011, p. 396—The Fluorescence Absorption and UV-VIS Spectra of Some Plant Extracts in Ethanol and in Polymeric Pluronic L64 Micelles.

Tsinghua Science and Technology, Shen Shufeng, et al., vol. 11, No. 2, 2006—Application of Block Copolymer in Three-Liquid-Phase Extraction System.

* cited by examiner

5% Fucus Vesiculosus Extraction In Water On Left And
Extraction 10% Pluronic F127/Water Solution On The Right.

METHODS FOR BOTANICAL AND/OR ALGAE EXTRACTION

This application takes the benefit of U.S. Provisional Application No. 61/656,221 filed Jun. 6, 2012, the contents herein incorporated entirely by reference.

BACKGROUND OF THE INVENTION

A. Field of the Invention

The present invention relates to methods for extraction of biomass. Biomass of most interest is that which contains biologically active extracts suitable for the skin treatment market. The biomass of interest includes botanicals (plants and bioferments thereof), algae (red, brown, green and red, including bioferments thereof), fungi and even animal (insect, crustacean) origin and the use of said extracts in cosmetic preparations prepared by the disclosed method.

These natural product hydrophobic extracts are often used in cosmetic and pharmaceutical application. Natural products, particularly botanically, fungi and algae derived such as flavonoids or flavonoid derivatives, have demonstrable beneficial properties on the skin and hair. For example, these extracts have demonstrated antimicrobial, antiseptic, anti-inflammatory, antioxidant, enzyme stimulation or inhibition, pigmentation enhancement or control, photoprotective, treatment of skin aging, skin imperfections, dry skin, photodamaged skin, wrinkles, age spots, acne, skin lightening, psoriasis, and atopic dermatosis.

The botanical, algae and fungal species are for example any botanical, algae or fungal species which may server as a source for flavonoid or flavonoid derivatives.

More particularly for example the biomass may be selected from but is not limited to the group consisting of: *Acacia senegal, Achillea millefolium, Aloe barbadensis, Ananus sativus, Argania spinosa, Avena sativa, Cassia alata, Cocoa Callus, Cocos nucifera, Bupleurum falcatum, Butyrospermum parkii, Calluna vulgaris, Camellia sinensis, Chondrus crispus, Centella asiatica, Ceratonia siliqua, Cestrum latifolium, Cinnamomum cassia, Citrus limon, Coffea Arabica, Cola acuminate, Cucumis sativus, Durio zibethinus, Glycine soja* (soybean), *Glycyrrhiza glabra, Gymnema sylvestre, Haslea ostrearia, Heliantus annuus, Hibiscus abelmoschus, Humulus lupulus, Laminaria digitata, Lepidium meyenii, Linum usitatissimum, Macadamia ternifolia, Malva sylvestris, Melissa officinalis, Morus alba, Morus bombycis, Nereocystis luetkeana, Olea europaea, Orthosiphon stamineus, Palmeria palmate, Peucedanum graveolens, Peumus boldus, Pisum sativum, Pueraria lobata, Punicia granatum, Pyrus malus, Rheum palmatum, Rhodiola crenulata, Rosmarinus officinalis, Saxifraga sarmentosa, Sarrcodiotheca gaudichaudii, Scutellaria baicalensis, Serenoa serrulata, Spirulina platensis, Theobroma cacao, Tuber magnatum, Uncaria tomentosa, Vitis vinifera, Ptychopetalum olacoides, Zea mays* and *Zingiber officinale*.

In particular extracts from algae are of special interest. For example, extraction of *Chondrus crispus, Nereocystic luetkeana* and *Sarrcodiotheca gaudichaudii, Fucus vesiculosus, Sarcodiotheca gaudichaudii, Ulva lactuca, Laminaria longicruris, Nannochloropsis oculata, Tetraselmis suecica* are of special interest.

Extracts from plants such as *Cassia alata, Argania spinosa* and *Cocoa Callus* are also of preferred interest.

B. Description of Related Art

Extracts may be obtained from the whole plant, algae or fungi (i.e., the entire plant is used to prepare the extract) or from a part of the plant (e.g., leaf, stem, root, flower, seed, sap, bark, etc.). The extracts can also be derived by fermentation which helps to break down the cellular tissue of the algae or plant, thereby possibly increasing the bioavailability of the naturally occurring bioactive targets.

During extraction typically more than one compound is extracted from the botanical or algae and will frequently range from at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 of differing extractants in a single composition.

The skin active targets of particular interest are the flavonoids and flavonoid derivatives.

Typically the plant (or any part of the plant such as the leaves, stems, bark, roots, fruit, flowers or flower buds, seeds, seed pods, sap, whole plant, etc.) is disrupted by mechanical means which results in a puree. The puree is then processed to be substantially free of impurities or undesired solids. The puree can then be poured into a shallow vessel and quickly exposed to low temperature, i.e., flash frozen, for example at −20 degrees centigrade or lower, preferably under a vacuum for removal of water content (lyophilization).

Aqueous, alcoholic, or oil based extraction techniques, or combinations thereof, have also been used in the past and are used on the whole plant or any part thereof of (e.g., leaves, stems, bark, roots, fruit, flowers or flower buds, seeds, seed pods, sap, whole plant, etc.) to produce an extract. In such a process, the desired part of the plant or the whole plant is crushed up (e.g., blender) and then extracted with the desired solvent (e.g., water, alcohol, water/alcohol, or oil based solvents) to obtain the desired extract. The extract can then be stored in liquid form, lyophilized, or subject to further processing techniques (e.g., heating, cooling, etc.). Extraction processes are well-known to those having ordinary skill in the extract field (e.g., maceration, infusion, percolation, digestion, decoction, hot continuous extraction, aqueous-alcoholic extract, counter current extract, microwave assisted extraction, ultrasound extraction, supercritical fluid extracts, phytonic extract (e.g., with hydro-fluoro-carbon solvents), etc.

It is known that certain surfactant water based systems may be used for extraction of various hydrocarbons. For example, Calvert, T. L. et al, AICHE Journal, (1994), Vol, 40, #9, p 1449-1457; Hurter, P. N. et. al. Langmuir 1992, 8, 1291-1299 teach the extraction of hydrocarbons from water waste systems.

Additionally, it is also known that some ethanol derived plant extracts can be solubilized in aqueous solutions containing poly(ethylene-oxide)-poly(propylene oxide) copolymers (V Dinoiu. et al, *Revista de Chimie*, 62/4, 396-400).

Further, U.S. Serial No. 2012/0010390 discloses the use of aqueous two phase systems for isolation of biomolecules or target compounds such as an antibody or a protein from a fermentation broth using ethylene oxide and propylene oxide random copolymers dissolved in one of the liquid phases. PCT application No. WO2012011589 discloses a method for the manufacturing of fat-soluble bioactive substances extracted from microbial cells using an organic solvent in combination with a surfactant.

There are however numerous disadvantages to extracting with solvents or even water especially when the extracts of interest are lipophilic, hydrophobic or amphiphilic. Although water is environmentally friendly, it is limited as an effective extracting solvent when the desired extractants are hydrophobic. Organic solvents are less desirable because of their possible flammability and environmental drawbacks. Furthermore, when the extractants are desired for use in cosmetics, in particular skin active cosmetics such as moisturizes etc., solvents are most undesirable because of their irritating or drying effects on skin. The organic solvent can usually be removed by evaporation but this is an additional step with related economic and environmental costs.

Further there is a need to retrieve more complex targeted biomass extracts which can be obtained through traditional aqueous, glycol or ethanol extractions and preferably accompanied by higher overall concentrations of the targeted extractants. It is of special importance that highly active skin benefit agents are extracted from the biomass such as for example flavonoids and flavonoid derivatives. These actives have been shown to be particularly effective in preventing radical damage on skin incurred from UV exposure and oxidation reactions.

Even though certain skin active targets are known to be secondary metabolites in numerous plants, algae and fungi, prediction of the activity of the total extracts on skin, for example activity in protection against UV and radical induced skin damage is much harder to predict. Changing the extraction medium may give rise to increased amounts of known protectants such as flavonoids but this change will also be impacted by the increase or decrease in unknown co-extractants which in turn may alter the activity of the total extractant on skin. Thus, the need for alternative extraction methods which not only increase the extraction of skin actives but do not negatively impact the overall effect of the total extractants is desired. It would also be highly desirable if the total composition of the extracts e gives overall better performance in protection of skin from the adverse effects of known skin harming agents such as ultraviolet rays, especially UV-B rays. In particular, it would be highly desirable to effectively partition the skin active target molecules without reliance on organic solvents and via an extraction method which achieves higher concentrations of targeted molecules. It would also be desirable for the partitioning matrix itself be suitable for cosmetic applications without further processing and for the partitioning matrix to protect the target molecules from oxidation and light degradation.

For certain biomass materials, extraction processes can retrieve cell toxic components as well as skin beneficial components as the partitioning occurs based on for example, solubility parameters. Thus typical extraction processes frequently do not adequately distinguish between the two (beneficial vs. toxic). The present inventors have found that the present process using the particular nonionic surfactants of interest in many instances excludes the toxic extractants from the total extractant.

Further, it is also highly desirable that the extraction process retrieves relatively low color extractants but still retrieves the important target molecules and that the total extracted materials have high beneficial activity on skin.

Additionally, the extraction process for biomass can be quite time consuming especially in relation to the filtering step (removal of the biomass). For example, aqueous extract of an algae biomass may take as long as three days and use multiple filters to remove the solid biomass from the extracting liquid. It would be highly desirable to improve this filtering step by speeding up the filtering process and the elimination of multiple filters.

Bottom: 5% algae extraction medium with butylene glycol
Fourth: 5% algae extraction medium with DI water.
Third: 5% algae extraction medium with 10 wt. % Pluronic® L44 in water.
Second: 5% algae extraction medium with 10 wt. % Pluronic® F68 in water.
Top: 5% algae extraction medium with 10 wt. % Pluronic® F127 in water.

Figure 2:
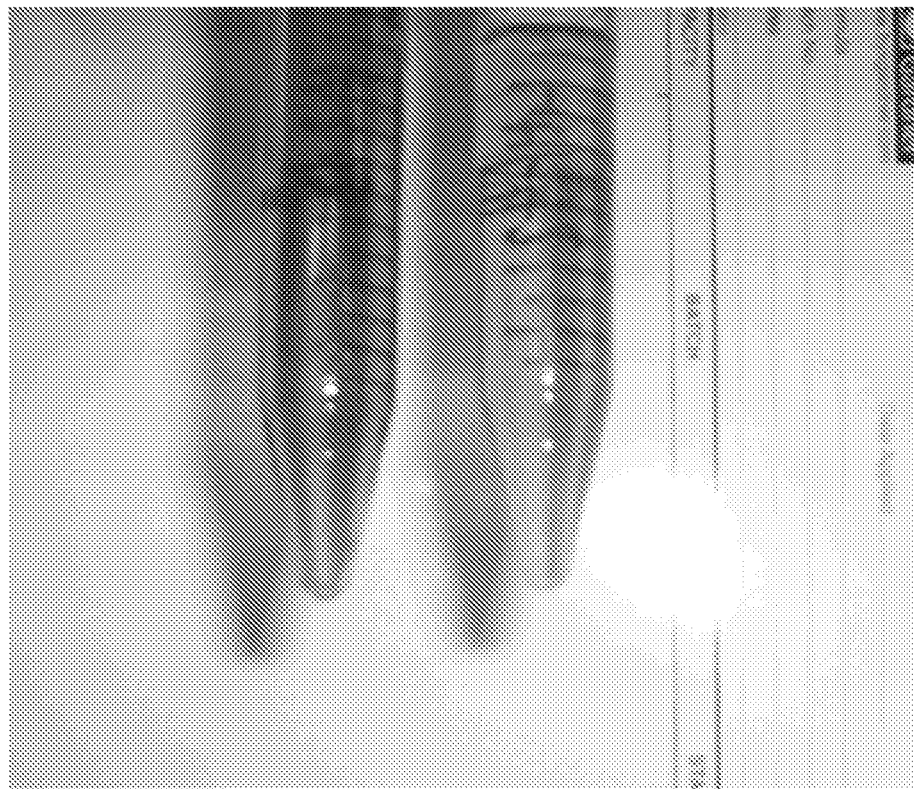

FIG. 2 is picture of *Fucus vesiculosus* extraction medium with:
Left—water extraction only.
Right—water and 10 wt. % Pluronic® F127 extraction.

SUMMARY OF THE INVENTION

The Applicants have devised a solution to many of the above difficulties by extracting the biomass using aqueous solutions of nonionic surfactants. The algae, fungi or botanical biomasses are easily extracted gaining significant efficiency benefits and overall improvements in the biologically active compounds extracted.

Other non-trivial advantages are apparent from the improved process such as color and odor improvements of the extractants. See FIG. 2. The avoidance of solvents such as alcohols and glycols can be eliminated entirely in the present process and the extractant medium presently employed is even milder than those currently in use containing glycols and/or ethanol. Gycols in particular are not popular with 'green' and sensitive skin companies.

Quite significantly the discovered method allows for much faster filtration and a reduction in the number of filtrations necessary to remove the extracted biomass from the aqueous extractant and surfactant solution. This equates to huge manufacturing cost savings.

Accordingly, the Applicants claim:

A method of extraction of at least one target skin bioactive from algae, fungi or botanical biomass, which method comprises a) contacting the algae, fungi or botanical biomass with an aqueous liquid to form a slurry,
   wherein the aqueous liquid comprises about 0.01 to about 20, preferably 0.1 to about 10, and most preferably about 0.5 to about 5 wt. percent, especially 0.5 to about 2 or about 3 wt. % of a nonionic surfactant selected from the group consisting of block copolymers of poly(ethylene oxide)/poly(propyleneoxide) and alkyl polyglucosides, and the wt. percent is based on the total weight of the slurry,
and
b) optionally, separating the biomass from the aqueous slurry,
wherein the target skin bioactive is a flavonoid or flavonoid derivative.

Use of a nonionic surfactant in an aqueous medium to increase flux during a filtration process of a solid biomass from an aqueous extract,
wherein the nonionic surfactant is a surfactant selected from the group consisting of block copolymers of poly(ethylene oxide)/poly(propyleneoxide) and alkyl polyglucosides and the aqueous extract comprises at least a flavonoid or flavonoid derivative.

The solid biomass is selected from algae, fungi or botanical biomass, preferably flavonoid rich biomass.

Use of a nonionic surfactant in an aqueous medium to increase the flavonoid extraction from a flavonoid rich plant, wherein the nonionic surfactant is a surfactant selected from the group consisting of block copolymers of poly(ethylene oxide)/poly(propyleneoxide) and alkyl polyglucosides.

DETAILED DESCRIPTION OF THE INVENTION

All percentages and ratios used herein are by weight of the total composition unless otherwise designated, and all temperatures are in degrees Celsius unless otherwise designated.

The term "safe and effective amount" as used herein means an amount of a compound or composition sufficient to induce a positive benefit as described herein, but low enough to avoid serious side effects in the judgment of the skilled artisan.

The term "slurry" as used herein means a suspension of plant, algae or fungi matter in water.

The term "molecular weight" as used herein refers to weight average molecular weight unless otherwise specified.

The term "comprising" for purposes of the invention is open ended, that is may include other components.

Plant, algae or fungi for purposes or this disclosure means any plant, algae or fungi, especially flavonoid rich plant, algae or funge. For example the plant, algae or fungi, preferably flavonoid rich plant, algae or fungi may be selected for example from the group of genus species consisting of *Acacia senegal, Achillea millefolium, Aloe barbadensis, Ananus sativus, Argania spinosa, Avena sativa, Cocos nucifera, Bupleurum falcatum, Butyrospermum parkii, Calluna vulgaris, Camellia sinensis, Cassia elate, Cocoa Callus, Chondrus crispus, Centella asiatica, Ceratonia siliqua, Cestrum latifolium, Cinnamomum cassia, Citrus limon, Coffee Arabica, Cola acuminate, Cucumis sativus, Durio zibethinus, Fucus vesiculosus, Glycine soja* (soybean), *Glycyrrhiza glabra, Gymnema sylvestre, Haslea ostrearia, Helianthus annuus, Hibiscus abelmoschus, Humulus lupulus, Laminaria digitate, Lepidium meyenii, Linum usitatissimum, Macadamia ternifolia, Melva sylvestris, Melissa officinalis, Morus alba, Morus bombycis, Nereocystis luetkeana, Olea europaea, Orthosiphon stamineus, Palmeria palmate, Peucedanum graveolens, Peumus boldus, Pisum sativum, Pueraria lobate, Punicia granatum, Pyrus malus, Rheum palmatum, Rhodiola crenulata, Rosmarinus officinalis, Saxifraga sarmentosa, Sarrcodiotheca gaudichaudii, Scutellaria baicalensis, Serenoa serrulata, Spirulina platensis, Theobroma cacao, Tuber magnatum, Uncaria tomentosa, Vitis vinifera, Ptychopetalum olacoides, Zea mays* and *Zingiber officinale*.

Any of the plants, algae or fungi used in the present disclosure may be natural occurring, cultivated or genetically modified organisms (GMO). For industrial cosmetic applications in the case of algae, it may be preferred to use cultivated algae, since cultivation reduces the risk that supplies will become limited in the case of algae as aquaculture expands and marine environmental conditions change.

The plant, algae or fungi source may be pre-treated in a fermentation process to further breakdown the plant, algae or fungi biomass pulp possibly making any bioactives present in the biomass more readily available for extraction.

For example, *Nereocystis* is genus of edible sea kelp that forms thick beds of up to 74 meter plants on rocks in what are known as kelp forests. This sea kelp may be fermented with *Lactobacillus*, the same bacterium that produces yogurt. Fermentation breaks down the cellular tissue of the kelp leaf, thereby increasing the bioavailability of the naturally occurring phytonutrients that are abundant in kelp.

Fermentation and subsequent reduction of the kelp extract may result in the concentration of these vital nutrients for use in topical formulations. In skincare products it acts as excellent oil-free moisturizer.

The term "biomass" as used herein means a pulp or puree derived from the algae, plant or fungi. Preferably the term biomass refers to an algae or plant. The pulp or puree may be derived from the entire plant, algae or fungi or from a part of the plant (e.g., leaf, stem, root, flower, seed, sap, bark, etc.).

The marine algae may for example be preferably selected from the group consisting of *Chondrus crispus, Nereocystic luetkeana* and *Sarrcodiotheca gaudichaudii, Fucus vesiculosus, Sarcodiotheca gaudichaudii, Ulva lactuca, Laminaria longicruris, Nannochloropsis oculata, Tetraselmis suecica*

The hydrophobic extracts from algae are especially interesting because the extracts are known to moisturize skin, have firming and anti-irritant properties which make the extracts highly suitable for aging skin. The algae extracts contain polysaccharide sugars such as alginates, fucoidanes, polyphenols and fucosterol. Alginates are compounds responsible for moisture retention and elasticity of the skin. Fucoidanes are sulfated polysaccharides that encourage circulation and polyphenols have antiseptic, anti-inflammatory and anti-oxidant properties. Fucosterol functions as a emollient, moisturizer and blood stimulant The term "extract" for purposes of this application means any skin active which has been extracted from the plant, algae or fungi biomass. In the present case, the extract is present in the extracting water/surfactant mixture. It is this mixture which is directly added to the cosmetic, topical or pharmaceutical product compositions. Indeed this is one of the advantages of the extracting method. The presence of the surfactant, in particular the Pluronic® does not need to be removed. It's presence in the final cosmetic, topical or pharmaceutical composition is desirable.

The extract will be present in the aqueous surfactant mixture liquid phase after extraction from the biomass.

Extraction for purposes of this application means treatment or exposure of the biomass (pulp or puree) with a liquid. Target bioactive moiety or moieties (at least one skin active) are retrieved from the solid biomass via solubilization in the liquid phase.

As explained previously the plant, algae or fungi is flavonoid rich. Extraction according to the presently disclosed methods of the flavonoid rich plant, algae or fungi will retrieve "target skin actives".

The term "target skin actives" to be extracted includes compounds containing the flavone backbone (2-phenyl-1,4-benzopyrone), isoflavone and the neoflavonoids backbones or derivatives thereof.

The flavone backbone is:

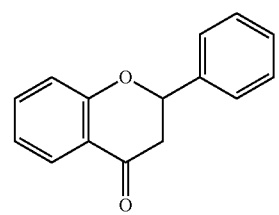

(A)

The isoflavan core is

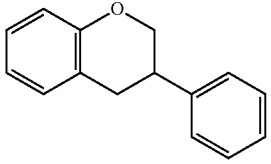
(B)

The neoflavonoid core is

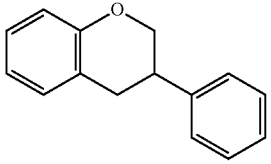
(C)

These above cores will normally be substituted by hydroxyl groups at various positions on the aromatic rings. In some cases such as myricitrin the oxygen containing ring is substituted by a sugar moiety. Accordingly the flavonoid or flavonoid derivative (the target skin actives) are selected from compounds which contain cores represented by (A), (B) and (C), the cores may be further substituted.

In terms of this disclosure what is meant by flavonoid-rich would preferably include plant, algae or fungi extract which contains flavonoids aglycones and or glycosides of flavones, of flavanones, of 3-hydroxyflavones (flavonoles), of aurones, and of isoflavones. Also preferred are biflavonoids constructed from two flavonoid units, for example, those occurring in ginkgo species. Further preferred flavonoids are the chalcones, especially phloricin, hesperidin methyl chalcone, and neohesperidin dihydrochalcone.

Accordingly a preferred listing of flavonoids would include abyssinone I, abyssinone V, afzelechin, ampelopsin, aromadendrin, asebogenin, auriculoside, betagarin, broussin, broussonin C, butin, butrin, (+)-catechin, catechin 7-O-β-xyloside, davidigenin, diffutin, 7,4'-dihydroxylflavan, 2,6-dihydroxyl-4'-methoxydihydro-chalcone, 7,3'-dihydroxyl-4'-methoxy-8-methylflavan, 7,4'-dihydroxyl-8-methylfalvan, 6,8-diprenylnaringenin, dracorubin, (−)-epicatechin, ent-epicatechen, epigallo catechin 3-gallate, eriocitrin, eriodictyol, farrerol, fisetinidol, fisetinidol-4-ol, fustin, garbanzol, glabranin, glepidotin β, glycyphyllin, hesperetin, hesperidin, homoeriodictyol, 7-hydroxyflavan, isochamaejasmin, isosakuranetin, isouriaretin, kazinol a, kolaflavanone, liquiretigenin, manniflavanone, 6, methocyaromadendrin 3-O-acetate, 6-methoxytaxifolin, 2'-O-methylodoratol, naringenin, naringin, narirutin, neoastilbin, neoeriocitrin, neohesperidin, odoratol, phloretin, phellamurin, phloretin, phloridzin, pinobanksin, pinocembrin, pinocembrin 7-rhamnosyl-glucoside, piperaduncin β, poncirin, 5'-prenyl, naringenin, pruning, sakuranetin, sanggenon C, sanggenon D, silandrin, silybin, silychristin, sophoranone, strobopinin, taxifolen, taxifolin-3-O-acetate, tephrowatsin, theasinensin A, 2',4',6'-trihydroxyl-3'-formyldihydrochalcone and uvaretin.

A more preferred list would include the flavonoids and flavonoid derivatives selected from the group consisting of naringin (aurantiin, naringenin 7-rhamnoglucoside), α-glucosylrutin, α-glucosylmyricetin, α-glucosylisoquercetin, α-glucosylquercetin, dihydroquercetin (taxifolin), hesperidin (3',5,7-trihydroxy-4'-methoxyflavanone 7-rhamnoglucoside, hesperitin 7-O-rhamnoglucoside), neohesperidin, rutin (3,3',4',5,7-pentahydroxyflavone 3-rhamnoglucoside, quercetin 3-rhamnoglucoside), troxerutin (3,5-dihydroxy-3',4',7-tris(2-hydroxyethoxy)flavone-3-(6-O-(6-deoxy-α-L-mannopyranosyl)β-D-glucopyranoside)), monoxerutin (3,3',4',5-tetrahydroxy-7-(2-hydroxyethoxy)flavone-3-(6-O-(6-deoxy-α-L-mannopyranosyl)β-D-glucopyranoside)), diosmin (3',4',7-trihydroxy-5-methoxyflavanone 7-rhamnoglucoside), eriodictin, and apigenin 7-glucoside (4',5,7-trihydroxyflavone 7-glucoside), kaempferol, quercitrin, avicularine, myricitin, epicatechins and catechins.

Extraction Method

As explained above the puree or pulp biomass is added to a water based medium to form a slurry.

The slurry will normally comprise primarily water, that is, comprise for example over 50 wt. %, more typically over 75 wt. %, most typically over 85 wt. % water but may further contain organic solvents.

The organic solvents may be hydrocarbons, fatty acid esters, ethers, alcohols, fatty acids or ketones. However, if organic solvents are used alcohols or polyalcohols are preferred and may be selected from the group consisting of methanol, ethanol, 1-propanol, 2-propanol, 1-butanol, 2-butanol, isobutyl alcohol, tert-butyl alcohol, 1,2-ethanediol, 1,2-propanediol, 1,3-propandiol, butylene glycol and glycerin. Preferably, no organic solvent is present in the extraction slurry.

Thus the slurry of step a) may comprise an organic solvent from about 1 to about 10 wt. percent of the slurry.

But the slurry is preferably essentially organic solvent free. By essentially organic solvent free, it is meant that the slurry contains minor amounts of organic solvent, that is about 0.1 to about 5 wt. percent, or 0.1 to about or less than 1 wt. percent organic solvent.

The slurry will contain about 0.01 to about 20, preferably 0.1 to about 10, and most preferably about 0.5 to about 5 wt. %, especially 0.5 to about 2 or about 3 wt. % of a nonionic surfactant, preferably the nonionic surfactant is a copolymer, preferably a block copolymer of poly(ethylene oxide) and poly(propylene oxide), or a alkyl polyglucoside and more preferably the nonionic surfactant is a triblock copolymer of poly(ethylene oxide) and poly(propylene oxide) or an alkyl polyglucoside.

The weight percent of the nonionic surfactant is based on the total weight of the slurry.

The term "hydrophobic" as used herein meant a component of the natural product (biomass) which is more soluble in a nonpolar solvent than in water.

Since many bioreactive or target molecules of the biomass are located within the structure of the cell wall or other organelles within the cell, a suitable process is required to extract the desired components from the cell. Accordingly, the cell wall barrier must be perturbed or ruptured sufficiently to allow diffusion to occur into the extraction liquid. A method is therefore needed to rupture cell walls and membranes to maximize the removal of the active. Examples of such process conditions include the use of heat, high sear mixing, ultrasonic waved, microwaves, high pressure and prolonged exposure to the extractant medium.

Thus the biomass is generally in the form of a pulp or puree which has been mashed or broken up to rupture cell walls and membranes.

The amount of pulp or puree biomass which is added to the extractant medium (water and nonionic surfactant) to form a slurry will vary from about 1 to about 50 wt. %, preferably about 2 to about 25 wt. % and most preferably about 3 to about 15 wt. % of the total weight of the slurry.

The pulp or puree biomass wt. % is normally a dry weight. For example, the pulp or puree is normally dried before extraction and most or all of the water content is removed. The weight percent of the dried biomass varies from about 1 to about 50 wt. % of the total weight of the slurry.

Therefore, the dried biomass contains, if any, only small amounts of water, for example 0.01 to 5 wt. %, preferably 0.01 to about 2 wt. % water.

Non-Ionic Surfactants

By "surfactant," it is meant any of those molecules that are commonly known in the art to provide a reduction in surface tension (such as being able to reduce the surface tension of water to 60 dynes/cm or less, and, more preferably 50 dynes/cm or less when added to pure deionized water, and measured at ambient temperature i.e., 20° C.). Furthermore, it is preferred that the surfactant or surfactants have a water solubility of at least about 1% in deionized water at ambient temperature. As such, the term surfactant can also include those molecules that are also commonly referred to as oil in water emulsifiers. In one embodiment, the non-ionic surfactant has a Hydrophile-Lipophile Balance (HLB) that is from about 8 to >24, and more preferably from about 10 to about >24.

By "non-ionic surfactant," it is meant a surfactant that does not ionize in aqueous media. In a preferred embodiment, the non-ionic surfactant is liquid at ambient temperature.

The function of the surfactant is to provide one or more of the following: emulsification or solubilization of hydrophobic compounds, wetting and surface tension reduction.

Non-ionic surfactants, which can be used in the presently disclosed extraction process, include those broadly defined as compounds produced by the condensation of alkylene oxide groups (hydrophilic in nature) with an organic hydrophobic compound, which may be aliphatic or alkyl aromatic in nature. Examples of preferred classes of nonionic surface-active agents are: the long chain alkanolamides; the polyethylene oxide condensates of alkyl phenols; the condensation product of aliphatic alcohols having from about 8 to about 18 carbon atoms, in either straight chain, block or branched chain configuration, with ethylene oxide; the long chain tertiary amine oxides; the long chain tertiary phosphine oxides; the long chain dialkyl sulfoxides containing one short chain alkyl or hydroxy alkyl radical of from about 1 to about 3 carbon atoms; and the alkyl polysaccharide (APS) surfactants such as the alkyl polyglycosides; the polyethylene glycol (PEG) glyceryl fatty esters and copolymers of ethylene oxide and propylene oxide including block copolymers of polyethylene oxide and polypropylene oxide. The preferred non-ionic surfactants are the condensation product of aliphatic alcohols having from about 8 to about 18 carbon atoms, in either straight chain, block or branched chain configuration, with ethylene oxide. For example, copolymers of ethylene oxide and propylene oxide are preferred.

Of special interest however are the block copolymers of polyethylene oxide and polypropylene oxide. These block copolymers are often referred to as poloxamers. These poloxamer surfactants are polymeric and comprise blocks of alternating hydrophobic and hydrophilic blocks. The hydrophobic blocks comprise polypropylene oxide while the hydrophilic blocks comprise polyethylene oxide blocks.

The poloxamers of interest in this application are diblock or triblock, preferably triblock poloxamers of the structures below and are known under the tradename Pluronic® supplied by BASF Corporation.

$$HO(C_2H_4O)_a(C_3H_6O)_b(C_2H_4O)_cOH \quad (I)$$

or $$HO(C_3H_6O)_b(C_2H_4O)_a(C_3H_6O)_dOH \quad (II)$$

wherein a and c are independently 3 to 200,
and b and d are independently is 5 to 100.

For example, some typical triblock polymers which are envisioned in the present application are:

| Pluronic ® | Molecular Weight |
|---|---|
| L10 | 3200 |
| L31 | 1100 |
| L35 | 1900 |
| L38 | 4700 |
| L42 | 1630 |
| L43 | 1850 |
| L44 | 2200 |
| L61 | 2000 |
| L62 | 2500 |
| L63 | 2650 |
| L64 | 2900 |
| P65 | 3400 |
| F68 | 8400 |
| L72 | 2750 |
| P75 | 4150 |
| F77 | 6600 |
| L81 | 2750 |
| P84 | 4200 |
| P85 | 4600 |
| F87 | 7700 |
| F88 | 11400 |
| L92 | 3650 |
| F98 | 13000 |
| L101 | 3800 |
| P104 | 5900 |
| P105 | 6500 |
| F108 | 14600 |
| L121 | 4400 |
| L122 | 5000 |
| P123 | 5750 |
| F127 | 12600 |
| RPE 1050 | 1950 |
| RPE 1720 | 2150 |
| RPE 1740 | 2650 |
| RPE 2520 | 3100 |
| RPE 2540 | 3600 |

Particularly preferred Pluronics® are Pluronic L35, L44, L43, P105, F68, F87, F108, RPE 1050, RPE 1720, RPR 1740 and F127 (NF Grades—BASF maintains a Drug Master File for some of these products).

$$*HO(C_2H_4O)_a(C_3H_6O)_b(C_2H_4O)_cOH \quad (I)$$

$$**HO(C_3H_6O)_b(C_2H_4O)_a(C_3H_6O)_dOH \quad (II)$$

| Pluronic ® | Poloxamer | a and c[1] | b and d[2] | Mw[3] | HLB |
|---|---|---|---|---|---|
| L35* | 101 | 11 | 16 | 1900 | 19 |
| L43* | 123 | 7 | 21 | 1850 | 7-12 |
| L44 * | 124 | 12 | 20 | 2090-2360 | 12-18 |
| F68* | 188 | 75 | 30 | 7680-9510 | >24 |
| F87* | 237 | 62 | 39 | 6840-8830 | >24 |
| F108* | 338 | 128 | 54 | 12700-17400 | >24 |
| P105* | 335 | 38 | 54 | 6500 | 12-18 |
| F127* | 407 | 98 | 58 | 9840-14600 | 18-23 |
| RPE 1050** | NA | 22 | 8 | ~1950 | 15 |

-continued

| Pluronic ® | Poloxamer | a and c[1] | b and d[2] | Mw[3] | HLB |
|---|---|---|---|---|---|
| RPE 1720** | NA | 10 | 15 | ~2150 | 6 |
| RPE 1740** | NA | 24 | 15 | ~2650 | 12 |

Note:
** and * designate whether formula (I) or (II) of the non-ionic surfactant.
[1] The number given in the table represents the number of repeating units in a and the number of repeating units in b. Accordingly for F108 of structure (I), a is 141 and c is 141.
[2] The number given in the table represents the number of repeating units of b and d. Accordingly for RPE 1050 of structure (II), a is 22 and b is 8 and d is 8.
[3] Mw represents weight average molecular weight.

The first step in synthesizing these Pluronic® surfactants is the creation of a hydrophobe of desired molecular weight by the controlled addition of propylene oxide to the two hydroxyl groups of propylene glycol. Ethylene oxide is then added to sandwich this hydrophobe between hydrophilic groups, controlled by length to constitute from 10% to 80% (by weight) of the final molecule.

In the RPE (or reverse Pluronic® surfactants) the structure is as in the formula II above. Thus the build up of the block copolymer is reversed. The central block is polyethylene oxide sandwiched between two polypropylene blocks.

A range of Pluronic® surfactants are available where the hydrophobe or center block (polypropylene oxide) varies from about 900 to 4000 weight average molecular weight and the ethylene oxide blocks make up from 10 to 80, preferably 30 to 95, most preferably 40 to 90 weight percent of the total block copolymer.

The reverse Pluronics® RPE surfactants are available where the center block (polyethylene glycol) weight average molecular weight varies from about 300 to about 1000 average molecular mass and the total weight average molecular weight for the polypropylene oxide terminal blocks range from about 1000 to about 3800.

Accordingly the triblock polymers typically range from about 1000 to about 16000 average molecular weight. The triblock polymers are liquid, solid or paste depending upon the molecular weight and the weight ratio of the hydrophobic (PP) and hydrophilic blocks (PE).

The inventors have discovered that a range of triblock copolymers of differing molecular weights and PP and PE ratios function when dissolved in aqueous solution are highly effective solubilizers for the target molecules from various plant, fungi and algae sources.

These particular block nonionic surfactants are known to form micelles in water. Thus they may function as solubilizing agents for target molecules.

Other non-ionic surfactants of particular interest are the alkyl polyglucoside.

Alkyl polyglucosides (APGs) are well known in the art and may be purchased under the tradename Plantaren® from BASF SE.

The terms alkyl polyglucoside and alkyl glucoside are interchangeable.

An alkyl polyglycoside is formed from the reaction of glucose and fatty alcohol. An alkyl polyglycoside compound has a hydrophobic portion (carbon chain) and a hydrophilic portion (glycoside unit or group). When describing an alkyl polyglycoside, the average degree of polymerization (DP) is mentioned. For example, in an alkyl polglycoside or alkyl glycoside a compound with a DP of about 1.4, there are, on average, 1.4 units of glucose for each alkyl group. An alkyl polyglucoside or alkyl glucoside is normally a mixture of varying amounts of glucose units on the molecule. It is to be understood that a DP of 1.4 does not mean that each molecule has 1.4 glucose units.

Alkyl polyglucosides may be represented by the following general formula: $R_1$—O—$(R_2O)_b$—$(Z)_a$ wherein $R_1$ is a monovalent organic radical having from about 6 to about 30 carbon atoms, $R_2$ is a divalent alkylene radical having from 2 to 4 carbon atoms, and Z is a saccharide residue having 5 or 6 carbon atoms, b is a number from 0 to about 12, and a is a number of from 1 to 6.

Additional suitable alkyl polyglucosides include, but are not limited to GLUCOPON® 225DK, in which the alkyl group contains 8 to 10 carbon atoms and has an average DP of 1.7; GLUCOPON® 625UP, in which the alkyl group has 12 to 16 carbon atoms and has an average DP of 1.6; APG® 325N, in which the alkyl group has 9 to 11 carbon atoms and has an average DP of 1.5; GLUCOPON® 600UP, in which the alkyl group has 12 to 16 carbon atoms and has an average DP of 1.4; PLANTAREN 2000®, in which the alkyl group has 8 to 16 carbon atoms and has an average DP of 1.5; and PLANTAREN 1300®, in which the alkyl group has 12 to 16 carbon atoms and an average DP of 1.6.

The alkyl polyglucosides is typically formed by reacting a sugar with a higher alcohol in the presence of an acid catalyst, or by reacting a sugar with a lower alcohol (for example, methanol, ethanol, propanol, butanol) to thereby provide a lower alkyl glycoside, which is then reacted with a higher alcohol. The higher alcohol generally has the formulation $R_1O(R_2O)_xH$, wherein $R_1$ represents a straight or branched alkyl or alkenyl group having from 8 to 22 carbon atoms, $R_2$ represents an alkylene group having from 2 to 20 carbon atoms, and $x$ is a mean value that is 0 to 10.

Specific non-limiting examples of the higher alcohol are straight or branched alkanol such as hexanol, heptanol, octanol, nonanol, decanol, dodecanol, tridecanol, tetradecanol, pentadecanol, hexadecanol, heptadecanol, octadecanol, methylpentanol, methylhexanol, methylheptanol, methyloctanol, methyldecanol, methylundecanol, methyltridecanol, methylheptadecanol, ethylhexanol, ethyloctanol, ethyldecanol, ethyldodecanol, 2-heptanol, 2-nonanol, 2-undecanol, 2-tridecanol, 2-pentadecanol, 2-heptadecanol, 2-butyloctanol, 2-hexyloctanol, 2-octyloctanol, 2-hexyldecanol and/or 2-octyldecanol; an alkenol such as hexenol, heptenol, octenol, nonenol, decenol, undecenol, dodecenol, tridecenol, tetradecenol, pentadecenol, hexadecenol, heptadecenol and octadecenol. These alcohols may be used either alone or a mixture of two or more of them.

Preferred alkyl glucosides comprise from about 1 to about 6 glucose residues per molecule, preferably 1 to 4. Preferred alkyl polyglucoside are decyl glucoside, caprylyl/capryl glucoside, coco glucoside and lauryl glucoside which are the condensation product of the corresponding alcohol with a glucose polymer or single glucose residue and is available commercially from BASF Corporation of Florham Park, N.J. under the trade name, Plantaren®.

The cosmetic compositions presently disclosed may further comprise various additives utilized in the cosmetic field. The CTFA Cosmetic Ingredient Handbook and Personal Care Product Counsels ingredient buyers guide describe a wide variety of nonlimiting cosmetic ingredients commonly used by those skilled in the art and which are suitable for use in the cosmetic compositions of the present invention. Examples of these ingredient classes included: abrasives, emulsifiers, absorbents, gelling agents, antifoaming agents, buffering agents, colorants, film formers, pH adjusters, humectants, thickeners and pigments. It is further recognized that additional cosmetic active ingredients, such as anti-acne actives (for example, salicylic acid or benzoyl peroxide), anti-wrinkle actives (for example, retinoids or beta-hydroxy acids), antioxidants (for example, ascorbic acid and its derivatives or tea extracts), chelators (for example, furildioxime), anti-inflammatory agents (for example, corticosteroids), slimming agents (for example, caffeine), skin lightening agents (for example, mulberry extract or kojic acid), or sunscreens (for example, those commercially available under the name PARSOL), may be utilized in the cosmetic compositions of the present invention based on the desired overall benefits intended to be conferred by the composition.

The upper and lower limits for the quantity of the extract according to the present invention in any given formulation for a cosmetic composition is based both on the desired effect of the cosmetic compositions, the other components of the formulation, the type of composition, cost and practicality. However, the plant, algae or fungi extract preferably is included in a quantity between about 0.01% and about 5% and more preferably between about 1% and 3% based on the final weight of the composition. For purposes of this application, this wt. % includes the extract, surfactant and water mixture.

Filtering of the Fungi, Algae or Biomass

Extracting with aqueous solutions of Pluronic® is faster and offers higher yields of extractant.

In order to remove the biomass, algae or fungi from the slurry it is often necessary to filter using increasingly smaller pore filters. For example, it is typical to require multiple filtrations starting from a large pore size of about 150 micron moving to progressively smaller pore sizes. For example, five filtrations may be necessary starting with 150 micron, followed by 11 micron, to 2.5 micron and finishing with 0.45 and 0.22 micron filters.

Another typical way of removing the extracted biomass is to centrifuge then filter the supernatant.

These consecutive filtrations are very time consuming. The filtration becomes progressively slower as the pore size decreases.

While the speed of filtration is to a certain extent biomass determined, if the extractant medium is water/Pluronic or an alkyl glucoside, it has been discovered that some of the intermediate filtrations can be eliminated. For example, one can move from a 2.5 micron filtration directly to a 0.45 filtration without going through an intermediate say 8.0 micron filtration. Of course, the elimination of extra filtration steps is highly desirable and one of the unexpected advantages of the present process.

Thus it has surprisingly been found that when the extractant medium is water/non-ionic surfactant or preferably water/Pluronic® or alkyl glucoside, the filtration process is significantly accelerated.

For example, when the inventive extractant medium is used, the filtering process is normally 2 or 3 time faster than an extractant medium comprising water only.

Accordingly the present method may embody the step of separating the plant, algae or fungi biomass from the aqueous liquid copolymer slurry by filtration and the filtration is carried out using a filter having a pore size ranging from about 0.1 to about 0.5 microns, preferably about 0.1 to about 0.4, most preferably about 0.1 to about 0.3 microns and the speed of filtration is at least twice as fast as separation of the plant, algae or fungi biomass from the same water or water/organic solvent slurry.

Use of the Extractant

The present extracts are particularly suitable for body care products, in particular for use in skin-care products, as bath and shower products, preparations containing fragrances and odoriferous substances (perfumes, after-shave lotions), hair-care products, deodorizing and antiperspirant preparations, decorative preparations, light protection formulations (sunscreens) and skin preparations containing active ingredients (vitamins, hormones or antimicrobials).

The extract is intended primarily for topical application to human skin or hair. The composition according to the invention is particularly useful as an agent for conditioning and smoothing the skin or hair, and preventing or reducing the appearance of wrinkled or aged skin and can thus be formulated into a topical skin treatment formulation for use in cosmetic applications. The topical skin treatment formulation of the invention is thus useful in the removal of oxidants from the skin and in the dermatological treatment of the skin including, but not limited to, skin imperfections, dry skin, photodamaged skin, wrinkles, age spots, acne, skin lightening, psoriasis, and atopic dermatosis.

Suitable skin-care products are, in particular, body oils, body lotions, body gels, treatment creams, skin protection ointments, shaving preparations, such as shaving foams or gels, skin powders, such as baby powder, moisturizing gels, moisturizing sprays, revitalizing body sprays, cellulite gels and peeling preparations.

Preparations containing fragrances and odoriferous substances are in particular scents, perfumes, toilet waters and shaving lotions (aftershave preparations).

Suitable hair-care products are, for example, shampoos for humans and animals, in particular dogs, hair conditioners, products for styling and treating hair, perming agents, hair sprays and lacquers, hair gels, hair fixatives and hair dyeing or bleaching agents.

Suitable decorative preparations for skin are for example lipsticks, nail varnishes, eye shadows, mascaras, dry and moist make-up, rouge, powders, depilatory agents and suntan lotions.

Suitable cosmetic formulations containing active ingredients are in particular hormone preparations, vitamin preparations, vegetable extract preparations and antibacterial preparations.

The present body care products can be in the form of creams, ointments, pastes, foams, gels, lotions, powders, make-ups, sprays, sticks or aerosols. The present extractants may be present in the oil phase or in the aqueous or aqueous/alcoholic phase.

The following examples further describe and illustrate the present invention and should not be construed as limitations of the present invention.

EXAMPLES

Example 1

Genus Species: *Nereocystis luetkeana*

*Nereocystis Luetkaeana* was provided by BC Kelp. The *N. luetkeana* is a dried, crushed pulp of all parts of the algae organism dried crushed material The above dried algae was added to various extractant mediums at the amounts given below in Table 1.

TABLE 1

Extraction Slurry Compositions for *N. Luetkaeana*

| DI Water | BG | Pluronic® L44 | Pluronic® F68 | Pluronic® F127 | Wt. % Algae |
|---|---|---|---|---|---|
| 95.00 | | | | | 5.00 |
| | 95.00 | | | | 5.00 |

TABLE 1-continued

Extraction Slurry Compositions for *N. Luetkaeana*

| DI Water | BG | Pluronic® L44 | Pluronic® F68 | Pluronic® F127 | Wt. % Algae |
|---|---|---|---|---|---|
| 85.00 | | 10.00 | | | 5.00 |
| 85.00 | | | 10.00 | | 5.00 |
| 85.00 | | | | 10.00 | 5.00 |

Notes:
numbers in % are w/w basis. Pluronics dissolved in water prior to addition of algae. BG refers to butylene glycol.

The above slurries are heated to 60° C. and mixed with high speed stirring for 1 hour. The slurry is cooled to room temperature and is filtered via 11 micron filter. Samples are filtered a second time through a 0.22 micron filter before analysis.

Example 2

Species: *Fucus vesiculosus*

A water only and water/Pluronic containing slurries were mixed overnight then filtered with a consecutively smaller pore size filters starting at 150 micron, 11 micron, 2.5 micron, 0.45, 0.22

TABLE 2

Extraction Slurry Compositions for *F. vesiculosus*

| DI Water | Pluronic® F127 | % Algae | % Yield[1] | Time to Filter[2] (hrs) |
|---|---|---|---|---|
| 95 | — | 5 | 30% | 6 |
| 85 | 10.00 | 5 | 50% | 1 |

[1]The % yield is a measure of the weight percent of the filtered extract collected after filtration. A higher yield would indicate less extract is lost during filtration.
[2]The water only extracting fluid slurry was filtered in sequence with consecutive filters used (pore size in um) = 150, 11, 2.5 and 0.8. The series of water only filtrations took 6 hours in total.

The water/Pluronic extracting fluid slurry was filtered in sequence with consecutive filters of pore sizes in microns 150, 11, 2.5, 0.45 and 0.22. The inventive extractions took a total of 2 hours. See FIG. 2 showing the difference in color of the extracting fluid.

Clearly incorporation of the Pluronic® within the aqueous media gave an improved extraction and filtering efficiency when compared with the water only. Extracting with aqueous solutions of Pluronic® is faster, of higher yield (almost double the yield at ⅓ the time).

Figure 1:
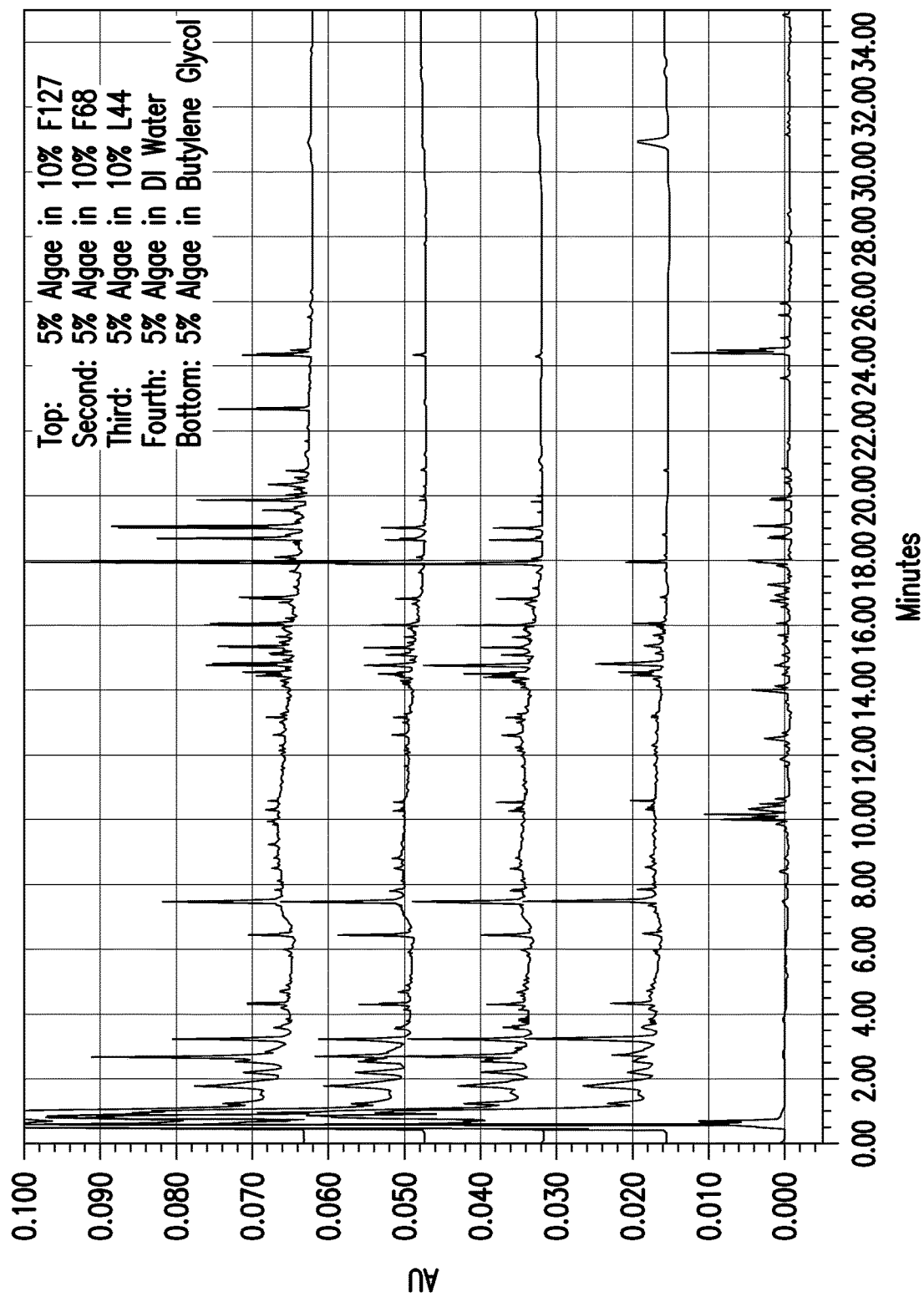
FIG. 1 is a comparison of extraction fingerprints from *Nereocystis luetkeana* using HPLC and different extraction mediums.

Analytical Results:

FIG. 1 is a comparison of extraction fingerprints from *Nereocystis luetkeana* using HPLC and different extraction mediums.

Pluronic extracts contained the same compounds as the 100% aqueous and butylene glycol extraction medium plus additional components.

FIG. 2 indicates that the color of extractant in the water/surfactant solution is of much better color when compared to the algae extracted with only water The extracts are thought to have antioxidant, anti-inflammatory, anti-melanogenic properties and perhaps collagen boosting properties. It is also believed that the surfactant-extract water mixtures are by themselves more oxidation resistant.

Table 3-7 Extractant Slurries for Additional Species

Aqueous extraction as above is carried out for a number of different plant species. The aqueous medium extractant only is compared to the extractant via aqueous medium containing varying amounts of non-ionic surfactants.

Dried, cut *Cassia alata* or *Argania spinosa* leaves were mixed with hot water (80° C.) or with the hot aqueous medium containing the non-ionic surfactants at a ratio of 1:9 (100 g leaves:0.9 L water), the pH of the mixture was adjusted to pH=6 and extraction was proceeded during 1 hour at 80° C., pH6 under shaking. After cooling to room temperature the insolubles were removed by centrifugation and the supernatant filtered. The concentration of the targeted flavonoids in each of the liquid extracts was measured (mg/100 g of liquid extract). The total amount of dry matter recovered in each extract was measured (g/100 g of liquid extract). The amount of active matter is calculated as the difference between the dry matter of the plant extract with surfactant medium and the dry matter of the surfactant solution alone.

Quantification of Flavonoids

Flavonoid determination in the liquid extracts were performed by HPLC analysis, the method depending of the flavonoids contained in the plant.

For *Cassia alata* leaves extracts, the column used was a C18 reversed phase column: Symmetryshield® RP 18 WATERS 5 µm (4.6×250 mm) maintained at 30° C. Gradient elution of the samples and standard were performed using water (eluent A) and acetonitrile (eluent B). The gradient elution initial conditions were 20% of eluent B with linear gradient to 60% from 0 to 35 min, followed by linear gradient to 20% of eluent B at 37 min.

The flow rate was 1 ml/min and the sample injection volume was 10 µl: 2 injections were performed for each sample Detection was performed with a Photo Diode Array Detector at 350 nm Calibration curves were realized with a Kaempferol 3-O-sophoroside and Kaempferol standards injected at different concentrations.

Biological Testing

Antiinflammatory Properties In Vitro-UVB Light Protection (UVB-LDH and UVB-PGE2)

Cell Protection Effect Against UVB on In Vitro Cultivated Human Keratinocytes

Background: UVB rays (from 280 to 320 nm) trigger inflammation (erythema, odema) by activating an enzyme, namely phospholipase A2 or PLA2, which removes arachidonic acid from the phospholipids of the plasma membrane. Arachidonic acid is the precursor of prostaglandins, which cause inflammation and cell membrane damage; the prostaglandins E2 (=PGE2) are formed by cyclooxygenase. This membrane stress is indicated by the release of the cytoplasm enzyme lactate dehydrogenase (LDH). The effect of UVB radiation was investigated on keratinocytes in vitro by determining the release of the cytoplasm enzyme LDH (lactate dehydrogenase). This enzyme serves as a marker for cell damage.

Method: To carry out the tests, a defined medium (DMEM), which comprises 10% fetal calf serum, was inoculated with the keratinocytes and the plant extract (diluted with saline solution) was added 72 hours after inoculation.

The keratinocytes were then irradiated with a UVB dose (30 mJ/cm$^2$-tubes: DUKE GL40E).

Following further incubation for 1 day at 37° C. and at 5% $CO_2$, the LDH and the PGE2 content in the supernatant was determined. The content of LDH (lactate dehydrogenase) was determined by means of an enzyme reaction (kit used to investigate the LDH content from Roche). The content of PGE2 was determined using an ELISA test (ELISA kit from Roche). Following trypsin treatment, the cells were centrifuged and counted.

Anti-Radical Action Testing

The oxidative anti-stress properties were evaluated by "in tubo" and "in vitro" tests.

The group of in tubo tests includes both the initial radical-type forms of oxygen and the reactive forms introduced in vivo: radical hydroxyl (HO and anion superoxide ($O_2$).

1) "Chemical" Tests in Tubo a) AO Antioxidant DPPH Test (AO-DPPH)

DPPH (diphenylpicryl hydrazyl) is a free, stable, violet-coloured radical which, in its leuco derivative, is modified by substances which capture free radicals (neutralising effect, also described as a "scavenger effect").

The result is given as percent inhibition of $DPPH^0$ in radical form relative to the control material without extract.

b) Anti-$HO^0$ Test with Salicylic Acid (Fenton Reaction)

The $HO^0$ (formed by $H_2O_2$ with Fe.sup.++ and EDTA present) hydroxylate the salicylic acid, which then forms a reddish compound.

The optical density at 490 nm corresponds to the hydroxylated salicylic acid content.

An anti-radical substance reacts with the $HO^0$ radicals and reduces the formation of this red compound.

The results are given as percent inhibition of the hydroxylation content (average of 2 tests).

Thiobarbituric Acid Reactive Assay (% AO-TBARS)

An In vitro model to test relative antioxidant potential: ultraviolet-induced lipid peroxydation in liposomes, *Archives of biochemistry and biophysics*, Vol. 283, No. 2, 234-240, (1990).

An approch towards understanding the genesis of sunlight-induced skin cancer, *Indian Journal of Biochemistry and Biophysics*, Vol. 27, 254-263, (1990).

Abbreviations

APG-1 is Plantacare® 2000 UP or Decyl Glucoside (INCI)
APG-2 is Plantacare® 810 UP or Caprylyl/Capryl Glucoside (INCI)
L35 is Pluronic® L35 or Poloxamer 101 (USAN)
L43 is Pluronic® L43 or Poloxamer 123 (USAN)
L44 is Pluronic® L44 or Poloxamer 124 (USAN)
NPE 1720 is a Pluronic® RPE 1720
P105 is Pluronic® P105 or Poloxamer 335 (USAN)
UVB-LDH LDH or lactate dehydrogenase determination by means of an enzyme reaction
UVB-PGE2 prostaglandins E2 determined using an ELISA test (ELISA kit from Roche).
% AO-DPPH—Anti-Radical test using diphenylpicryl hydrazyl
% AO-TBARS—Thiobarbituric Acid Reactive Assay—See above.

TABLE 3

Extracts of *Cassia alata* leaves with quantification of flavonoids

| | Surfactant | Surfactant Wt. %. | Active Matter (g/100 g) | Kaempferol-3-O-sophoroside (K3OS) (mg/100 g of liquid extract) | Kaempferol (mg/100 g of liquid extract) |
|---|---|---|---|---|---|
| Cassia alata extracts | None (water) | 0 | 3.59 | 225 | 0 |
| | APG-1 | 1 | 3.65 | 217 | — |
| | APG-2 | 5 | 3.86 | 220 | 3.6 |
| | L35 | 10 | 3.67 | 269 | 9.1 |
| | L43 | 10 | 3.80 | 272 | 11.3 |
| | L44 | 10 | 4.31 | 268 | 19.7 |
| | RPE1720 | 10 | 2.35 | 217 | 0 |
| | P105 | 10 | 4.85 | 286 | 26.6 |

TABLE 4

Comparison of anti-UVB activities between water and aqueous medium containing non-ionic surfactants extracts of *Cassia alata* leaves (all liquid extracts were tested at a 0.5% dilution)

| Species | Extract | Wt. % Surf | LDH (U/mg protein) | PGE2 (pg/well) |
|---|---|---|---|---|
| Cassia alata extracts | Control without UV | | 0 | −4 |
| | Control with UV | | 100 | 100 |
| | Positive control (aspirin at 0.03%) | | 15 | −6 |
| | Water | | 42 | 29 |
| | APG-1 | 1 | NT | NT |
| | APG-2 | 5 | 118 | 34 |
| | L35 | 10 | 52 | 18 |
| | L43 | 10 | 41 | 1 |
| | L44 | 10 | 29 | 2 |
| | NPE1720 | 10 | 140 | 15 |
| | P105 | 10 | 4 | −1 |

TABLE 5

Extracts of *Argania spinosa* leaves with quantification of flavonoids

| Species | Surfactant | Surfactant Wt. %. | Active Matter (g/100 g of liquid extract) | Myricitrin (mg/100 g of liquid extract) | Quercitrin (mg/100 g of liquid extract) |
|---|---|---|---|---|---|
| Argania spinosa Leaves extracts | None (water) | 0 | 4.27 | 37.9 | 24.4 |
| | APG-1 | 1 | 4.08 | 38.2 | 23.9 |
| | APG-2 | 5 | 4.63 | 46.9 | 32.8 |
| | L35 | 10 | 3.37 | 55.4 | 35.4 |
| | L43 | 10 | 2.16 | 50.4 | 31.0 |
| | L44 | 10 | 2.90 | 53.6 | 33.5 |
| | RPE1720 | 10 | 1.42 | 35.3 | 19.1 |
| | P105 | 10 | 6.29 | 76.0 | 52.4 |

TABLE 6

Comparison of anti-UVB activities between water and aqueous medium containing non-ionic surfactants extracts of *Argania spinosa* leaves (all liquid extracts were tested at a 0.037% dilution)

| Species | Surfactant | Surfactant Wt. %.. | LDH (U/mg protein) | PGE2 pg/well |
|---|---|---|---|---|
| | Control without UV | | 0 | 0 |
| | Control with UV | | 100 | 100 |
| | Positive control (aspirin at 0.03%) | | 0 | 0 |
| *Argania spinosa* Leaves extracts | None (water) | 0 | 79 | 58 |
| | APG-1 | 1 | 86 | 84 |
| | APG-2 | 5 | 48 | 42 |
| | L35 | 10 | 78 | 55 |
| | L43 | 10 | 56 | 23 |
| | L44 | 10 | 81 | 33 |
| | RPE1720 | 10 | 86 | 52 |
| | P105 | 10 | 4 | 0 |

The dry weight of the plant species in all cases is 5 wt. % of the total slurry weight in Table 7. The slurries are stirred for 1-2 hours at room temperature before measurements are taken for grams of active extractant per 100/g of liquid, flavonoid concentration and biological testing.

TABLE 7

Extracts of *Cacao alata* with quantification of flavonoid and corresponding biologic activity

| Species | Surfactant | Wt. % Surf. | Extract[1] (g/100 g) | Kaempferol (% var. vs. H2O ext.) | UVB-LDH | UVB-PGE |
|---|---|---|---|---|---|---|
| *Cacao alata* | None (water) | | 0.22 | 0 | 42 | 29 |
| | APG-1 | 1 | 0.10 | neg. | | |
| | APG-2 | 1 | 0.10 | neg. | 118 | 34 |
| | L35 | 10 | 0.25 | 19.40 | 52 | 18 |
| | L43 | 10 | 0.39 | 20.72 | 41 | 1 |
| | L44 | 5 | 0.32 | 19.12 | 29 | 2 |
| | NPE1720 | 1 | 0.33 | neg. | 140 | 15 |
| | P105 | 1 | 0.15 | 2.7 | 4 | neg. |

Formulation Examples

Example 1A

Purifying Toner for Skin

| Ph. | Trade Name | INCI Name | % wt |
|---|---|---|---|
| A | Deionized Water | Water | 89.40 |
| | Glycerin | Glycerin | 3.00 |
| | Elestab ® 388 | Propylene Glycol (and) Phenoxyethanol (and) Chlorphenesin (and) Methylparaben | 1.00 |
| | D-Panthenol 75 W | Panthenol | 0.50 |
| B | Eumulgin ® HPS | Coceth-7 (and) PPG-1-PEG-9 Lauryl Glycol Ether (and) PEG-40 Hydrogenated Castor Oil | 1.50 |
| | Copherol ®1250 C | Tocopheryl Acetate | 0.50 |

Purifying Toner for Skin (continued)

| Ph. | Trade Name | INCI Name | % wt |
|---|---|---|---|
| | Ocean Breeze 6110736[1] | Fragrance | 0.10 |
| C | Mat-XS ™ Clinical | Water (and) Butylene Glycol (and) Xanthan Gum (and) Sarcosine | 2.00 |
| | Extract according to invention | Exact (and) water (and) nonionic surfactant | .01-5 |
| | TEA 99% | Triethanolamine | q.s. |

Supplier Footnotes:
[1]Bell Flavors and Fragrances

Procedure

While stirring Phase A, add premixed Phase B. Then add Phase C one by one, and mix well between additions.

Example 2A

Day Cream with Naturally Sourced UV Protection

| Ph. | Trade Name | INCI Name | % wt |
|---|---|---|---|
| A | Deionized Water | Water | q.s. |
| | Edeta ® BD | Disodium EDTA | 0.10 |
| | D-Panthenol ® 75 W | Panthenol | 0.75 |
| B | Glycerin | Glycerin 99% | 2.00 |
| | Keltrol CG[1] | Xantham Gum | 0.20 |
| | Veegum Ultra[2] | Magnesium Aluminum Silicate | 0.40 |
| C | Lanette ® 22 | Behenyl Alcohol | 2.00 |
| | Eumulgin ® SG | Sodium Stearoyl Glutamate | 0.75 |
| | Myritol ® 331 | Cocoglycerides | 3.50 |
| | Emuigade ® PL 68/50 | Cetearyl Glucoside (and) Cetearyl Alcohol | 3.50 |
| | Cetiol ® SB 45 | Butyrospermum Parkii (Shea) Butter | 1.50 |
| | Cetiol ® OE | Dicaprylyl Ether | 3.00 |
| D | Z-COTE® LSA | Zinc Oxide (and) Triethoxycaprylysilane | 12.50 |
| | Cetiol ® RLF | Caprylyl Caprylate/Caprate | 7.00 |
| | Cetiol ® CC | Dicaprylyl Carbonate | 7.50 |
| E | Sensiva SC 50[3] | Ethylhexylglycerin | 1.00 |
| | Marine Filling Spheres | Pentaerytrityl Tetraisostearate (and) Silica Dimethyl Sylilate (and) Sodium Chondroitin Sulfate (and) Extract according to the invenion | 1.00 |
| | Ocean Breeze 6110736[4] | Fragrance | 0.10 |
| | Citric Acid 25% Sol. | Citric Acid | q.s. |

Supplier Footnotes:
[1]C.P. Kleco
[2]RT Vanderbilt
[3]Shulke
[4]Intarone

Procedure

Combine Phase A and start heating to 75-80 C. Premix Phase B and add to Phase A while heating to 75-80 C. Combine Phase C and heat to 75-80 C. Combine Phase D homogenize until uniform then add to Phase C and continue heating to 75-80 C. Add Phase C/D to Phase A/B while homogenizing until uniform. Transfer to sweep mixing and start cooling to 40 C. Add Phase E ingredients one by one and mix well between additions. Cool to room temperature and stop.

Example 3A

Moisturizing Makeup Removing Wipe

| Ph. | Trade Name | INCI Name | % wt |
|---|---|---|---|
| A | Deionized Water | Water | q.s. to 100 |
|  | Emulgade ® CM | Cetearyl Isononanoate (and) Ceteareth-20 (and) Cetearyl Alcohol (and) Glyceryl Stearate (and) Glycerin (and) Ceteareth-12 (and) Cetyl Palmitate | 6.00-10.00 |
|  | Extract according to the Invention | Extract according to the invention | .01-5.00 |
|  | Citric Acid (50% Soln) | Citric Acid | 0.10 |
|  | Fragrance | Fragrance | q.s. |
|  | Preservative | Preservative | q.s. |

Viscosity [mPas]: Brook. RVF, 23° C., spindle 4, 10 rpm. pH: 4.9-5.1

Example 4A

Night Cream

| Ph. | Trade Name | INCI Name | % wt |
|---|---|---|---|
| A | Deionized Water | Water | 65.15 |
|  | Elestab 388 | Propylene glycol (and) Phenoxyethanol (and) Chlorphenesin (and) Methylparaben | 1.00 |
| B | Glycerin | Glycerin | 3.00 |
|  | Vanzan NF[1] | Xanthan gum | 0.10 |
|  | Cosmedia ® SP | Sodium Polyacrylate | 0.70 |
| C | Emulgade ® Sucro | Sucrose Polystearate (and) Hydrogenated Polyisobutene | 3.00 |
|  | Eumulgin ® SG | Sodium Stearoyl Glutamate | 1.00 |
|  | Cutina ® HVG | Hydrogenated Vegetable Glycerides | 4.00 |
|  | Monomuls ® 90-O 18 | Glyceryl Oleate | 0.50 |
|  | Cetiol ® RLF | Caprylyl Caprylate/Caprate | 3.00 |
|  | Myritol ® 312 | Caprylic/ Capric Triglycerides | 6.00 |
|  | Cetiol ® J600 | Oleyl Erucate | 6.00 |
|  | Generol ® R | Brassica Campestris (Rapeseed) Sterols | 0.50 |
|  | Dow Corning 200 Fluid 350 cSt[2] | Dimethicone | 1.00 |
| D | Hyalufix ™ GL | Water (and) Butylene Glycol (and) Alpinia Galanga Leaf Extract (and) Xanthan Gum (and) Caprylic/Capric Triglyceride | 3.00 |
|  | Extract according to the invention | Extract (and) Xanthan Gum | 2.00 |
|  | Lavender Vanilla F-127981[3] | Frangrance | 0.05 |

Viscosity: Brookfield RVT, 23° C., spindle T-E @ 5 rpm: 180,000 cps pH: 6.3
Supplier Footnotes:
[1]RT Vanderbilt, Inc
[2]Dow Corning Corp.
[3]Intarome Fragrance and Flavor Corp.

Procedure

Premix Phase B and swell the mixture in the water Phase of Phase A. Then heat to 85 C. Heat Phase C to 85 C and mix until homogeneous. While stirring add Phase C to Phase A/B. Allow the emulsion to cool while stirring in such a way that it remains in continual motion. Avoid incorporating air. If necessary homogenize with a suitable dispersion unit (like Ultra Turrax) at approx. 65-60 C. When mixture cools to below 50 C, add Phase D while mixing. Stir while cooling until reaches room temperature.

Example 5A

Skin Serum

| Ph. | Trade Name | INCI Name | % wt |
|---|---|---|---|
| A | Deionized Water | Water | 84.7 |
|  | Glycerin | Glycerin | 3.00 |
|  | Elestab 388 | Propylene Glycol (and) Phenoxyethanol (and) Chlorphenesin (and) Methylparaben | 1.00 |
| B | Cosmedia ® SP | Sodium Polyacrylate | 0.80 |
| C | Cetiol ® Sensoft | Propylheptyl Caprylate | 3.00 |
|  | Eutanol ® G 16 S | Hexyldecyl Stearate | 2.00 |
|  | Cetiol ® 868 | Ethylhexyl Stearate | 2.00 |
| D | Actiwhite ™ LS 9808 | Water (and) Glycerin (and) Sucrose Dilaurate (and) Polysorbate 20 (and) Pisum Sativum (Pea) Extract | 3.00 |
|  | Extract according to the invention | Water (and) Extract | 2.00 |
|  | Bisabolol Natural | Bisabolol | 0.50 |

Viscosity: Brookfield RVT, 23° C., spindle T-C @ 10 rpm, with Helipath: 12000 cpspH: 5.80

Procedure

Mix Phase A and while stirring, slowly add Phase B to Phase A. When Phase B completely swells, add each ingredient of Phase C one at a time into the gel Phase. When completely mixed, add Phase D ingredients one at a time.

Example 6A

After-Sun Gel for Sensitive Skin

| Ph. | Trade Name | INCI Name | % wt |
|---|---|---|---|
| A | Dehyquart ® F75 | Distearoylethyl Hydroxyethylmonium Methosulfate (and) Cetearyl Alcohol | 0.70 |
|  | Emulgade ® Sucro | Sucrose Polystearate (and) Hydrogenated Polyisobutene | 0.50 |
|  | Cutina ® PES | Pentaerythrityl Distearate | 1.00 |
|  | Cutina ® GMS V | Glyceryl Stearate | 1.00 |
|  | Cetiol ® Sensoft | Propylheptyl Caprylate | 3.00 |
|  | Myritol ® 331 | Cocoglycerides | 2.00 |
|  | Cyperus Root Oil | Cyperus Esculentus Root Oil | 2.00 |
|  | Cosmedia ® Triple C | Polyquaternium-37 (and) Dicaprylyl Carbonate (and) Lauryl Glucoside | 1.50 |
| B | Glycerin | Glycerin | 3.00 |
|  | Elestab ® 388 | Propylene Glycol (and) Phenoxyethanol (and) Chlorphenesin (and) Methylparaben | 1.00 |
|  | Deionized Water | Water | 77.70 |
| C | Extract according to the invention | Water (and) Extract | 1.00 |
|  | Skinasensyl ™ PW LS 9852 | Mannitol (and) Sodium Citrate (and) Acetyl Tetrapeptide-15 | 0.30 |
|  | Ethanol | Ethanol | 5.00 |
| D | NaOH (10%) | Sodium Hydroxide | q.s. |
|  | Floral Plumeria F-127985[1] | Fragrance | 0.30 |

Viscosity: Brookfield RVT, 23° C., spindle T-E @ 5 rpm, with Helipath: 120,000 cps pH: 4.0-4.5
Supplier Footnotes:
[1]Intarome Fragrance and Flavor Corp.

Procedure

Heat Phase A and B separately to 80-85 C. Add Phase B to A. under moderate mixing. Start cooling. Add Phase C at 45 C or below and mix well between each addition. Add Phase D one by one, mix well between additions, than cool to room temperature and stop.

Example 7A

No-Foam Cleanser

| Ph. | Trade Name | INCI Name | % wt |
|---|---|---|---|
| A | Eumulgin ® VL 75 | Lauryl Glucoside (and) Polygercyl-2 Dipolyhydroxystearate (and) Glycerin | 1.50 |
|  | Cutina ® HVG | Hydrogenated Vegetable Glycerides | 1.50 |
|  | Cutina ® PES | Pentaerythrityl Distearate | 1.00 |
|  | Cetiol ® CC | Dicaprylyl Carbonate | 3.00 |
|  | Luvitol ® Lite | Hydrogenated Polyisobutane | 3.00 |
|  | Myritol ® 331 | Cocoglycerides | 2.00 |
|  | Cosmedia ® SP | Sodium Polyacrylate | 0.80 |
| B | Deionized Water | Water | 80.65 |
|  | Glycerin | Glycerin | 3.00 |
|  | Elestab ® 388 | Propylene Glycol (and) Phenoxyethanol (and) Chlorphenesin (and) Methylparaben | 1.00 |
|  | Horse Chestnut Extract | Mannitol (and) Ammonium Glycyrrhizate (and) Caffeine (and) Zinc Gluconate (and) Aesculus Hippocastanum (Horse Chestnut) Seed Extract | 1.00 |
|  | NaOH (10%) | Sodium Hydroxide (and) Water | q.s. |
| C | Extract according to the invention | Water (and) Extract | 1.50 |
|  | Champagne Petals RU-2133[1] | | 0.05 |

Viscosity: Brookfield RVT, 23° C., spindle T-E @ 5 rpm, with Helipath: 61,000 cps pH: 6.0

Supplier Footnotes:

[1] Takasago International Corp.

Procedure

Combine Phase A, without Cosmedia SP and heat to 80-85 C. Sprinkle Cosmedia SP into Phase A while at 80-85 C and mix well. Combine Phase B and heat to 80-85 C. Add Phase B to Phase A while at 80-85 C and mix well. Start cooling, and homogenize at 55-60 C. Add Phase C at 40 C or below one by one and mix well between additions. Cool to room temperature and stop.

Example 8A

Eye Cream

| Ph. | Trade Name | INCI Name | % wt |
|---|---|---|---|
| A | Emulgade ® SE-PF | Glyceryl Stearate (and) Ceteareth-20 (and) Ceteareth-12 (and) Cetearyl Alcohol (and) Cetyl Palmitate | 5.00 |
|  | Emulgade ® PL 68/50 | Cetearyl Glucoside (and) Cetearyl Alcohol | 2.00 |
|  | Cetiol ® RLF | Caprylyl Caprylate/Caprate | 5.00 |
|  | Cetiol ® MM | Myristyl Myristate | 0.50 |
|  | Cetiol ® SB 45 | Butyrospermum Parkii (Shea) Butter | 1.00 |
|  | Cetiol ® Sensoft | Propylheptyl Caprylate | 2.00 |
|  | Eutanol ® G | Octyldodecanol | 2.00 |
|  | Covi-ox ® T 70 C | Tocopherol | 0.50 |
|  | Dow Corning 200 Fluid 350 cSt[1] | Dimethicone | 0.50 |
|  | Cosmedia ® SP | Sodium Polyacrylate | 0.50 |
|  | Vanzan NF[2] | Xanthan Gum | 0.20 |
| B | Deionized Water | Water | 70.70 |
|  | Glycerin | Glycerin | 3.00 |
|  | Elestab ® 388 | Propylene Glycol (and) Phenoxyethanol (and) Chlorphenesin (and) Methylparaben | 1.00 |
| C | AMC ™ | Glycerin (and) Water (and) Sodium PCA (and) Urea, (and) Trehalose (and) Triacetin (and) Sodium Hyaluronate (and) Polyquaternium-51 | 3.00 |
|  | Extract according to the invention | Water (and) Extract (and) Xanthan Gum | 3.00 |
|  | Champagne Petals RU-2133[3] | | 0.10 |

Viscosity: Brookfield RVT, 23° C., spindle T-E @ 5 rpm, with Helipath: 30,000 cps pH: 6.0

Supplier Footnotes:

[1] Dow Corning Corporation

[2] RT Vnaderbilt, Inc

[3] Takasago International Corp.

Procedure

Heat Phase A (without Cosmedia SP and Xanthan Gum) and Phase B to 80-85 C. While stirring Phase A, disperse Cosmedia SP and Xanthan Gum.

Combine and heat Phase B to 80-85 C then add to Phase A, while mixing.

Start cooling. Homogenize at 55-60 C. Add Phase C one by one at 40 C or below, mix well between additions, then cool to room temperature and stop.

Example 9A

Skin Firming Lotion

| Ph. | Trade Name | INCI Name | % wt |
|---|---|---|---|
| A | Deionized Water | Water | 68.40 |
|  | Glycerin | Glycerin | 3.00 |
|  | Elestab ® 388 | Propylene Glycol (and) Phenoxyethanol (and) Chlorphenesin (and) Methylparaben | 1.00 |
|  | Vanzan NF | Xanthan Gum | 0.10 |
|  | Cosmedia ® SP | Sodium Polyacrylate | 1.00 |
| B | Plantapon ® LGC Sorb | Sodium Lauryl Glucose Carboxylate (and) Lauryl Glucoside | 1.50 |
| C | Dehymuls ® PGPH | Polyglyceryl-2 Dipolyhydroxystearate | 4.00 |
|  | Cetiol ® Sensoft | Propylheptyl Caprylate | 5.00 |
|  | Myritol ® 331 | Cocoglyceride | 3.00 |
|  | Cetiol ® J600 | Oleyl Erucate | 1.00 |
|  | Cetiol ® SB 45 | Butyrospermum Parkii (Shea) Butter | 2.00 |
| D | Champagne Petals RU-2133 | | 3.00 |
| E | Extract according to the invention | Water (and) Extract | 2.00 |
|  | Baobab Extract | Hydrolyzed Adansonia Digitata Extract | 5.00 |

Viscosity: Brookfield RVT, 23° C., spindle #5 @ 10 rpm: 7,800 cps pH: 5.5

Supplier Footnotes:

[1] RT Vanderbilt, Inc

[2] Takasago International Corp.

Procedure

Swell pre-mixed Cosmedia SP and Vanzan NF in Phase A. Add Phase B and mix homogeneously. Heat Phase C to 45-50 C—just enough to melt shea butter. Mix homogeneously and cool to room temp. Add Phase D to Phase C and mix well.

Then slowly add oil Phase C/D to the water Phase A/B while stirring. Avoid incorporating air. If necessary homogenize with a suitable dispersion unit (e.g. Ultra Turrex).

Add ingredients in Phase E one by one while mixing.

Example 10A

Body Lotion

| Ph. | Trade Name | INCI Name | % wt |
|---|---|---|---|
| A | Emulgade ® PL 68/50 | Cetearyl Glucoside (and) Cetearyl Alcohol | 5.00 |
|  | Cutina ® CP | Cetyl Palmitate | 3.00 |
|  | Monomul s® 90-O 18 | Glyceryl Oleate | 0.50 |
|  | Cetiol ® OE | Dicaprylyl Ether | 2.00 |
|  | Myritol ® 312 | Caprylic/Capric Triglyceride | 5.00 |
|  | Cegesoft ® PS 6 | Vegetable Oil | 4.00 |
|  | Cegesoft ® VP | Vegetable Oil (and) Hydrogenated Vegetable Oil (and) *Euphorbia Cerifera* (Candelilla) Wax | 1.00 |
| B | Deionized Water | Water | 74.15 |
|  | Vanzan NF (RT Vanderbilt)[1] | Xanthan Gum | 0.50 |
|  | Glycerin | Glycerin | 3.00 |
|  | Potassium Sorbate[2] | Potassium Sorbate | 0.30 |
|  | Elestab ® CPN | Chlorphenesin | 0.25 |
|  | Eumulgin ® SG | Sodium Stearoyl Glutamate | 1.00 |
| C | Extract according to the invention | Extract (and) Pluronic ® | 0.20 |
|  | Bergamot & Jasmine Musk F-127986[3] |  | 0.10 |
|  | Citric Acid (25%) | Citric Acid | q.s. |

Viscosity: Brookfield RVT, 23° C., spindle T-E @5 rpm: 40,000 cps pH: 6.4
Supplier Footnotes:
[1]RT Vanderbilt, Inc
[2]Jeen International Corporation
[3]Inatome Fragrance and Flavor Corp Procedure Prepare Phase B. Hydrate the thickeners first, then add the rest of the ingredients while mixing. Heat Phase A and B to 80-85 C. Add Phase B to Phase A, then cool to 55-60 C and homogenize. Transfer to regular mixing and continue cooling. Add Phase C one by one at 40 C or below and mix well between additions. If necessary adjust pH with citric acid.

Example 11A

Lipstick or other anhydrous product type

| Phase | Ingredient | Wt. % (w/w) |
|---|---|---|
| A | Mineral wax | 17.0 |
|  | Isostearyl isostearate | 31.5 |
|  | Propylene glycol dipelargonate | 2.6 |
|  | Propylene glycol isostearate | 1.7 |
|  | PEG 8 beeswax | 3.0 |
|  | Hydrogenated palm kernel oil, glycerides, hydrogenated palm glyceride | 3.4 |
|  | Lanolin oil | 3.4 |
|  | Sesame oil | 1.7 |
|  | Tribehenin | 1.7 |
|  | Cetyl lactate | 3.0 |
|  | Mineral oil, lanolin alcohol | 3.0 |
| B | Castor oil | qsp 100 |
|  | Titanium dioxide | 3.9 |
|  | CI 15850:1 | .616 |
|  | CI 45410:1 | .256 |
|  | CI 19140:1 | .048 |
|  | CI 77491 | 1.048 |
| C | Extract according to invention | .001-5 |

The invention claimed is:

1. A method of extraction of at least one target skin bioactive from algae, fungi or botanical biomass, which method comprises:
    a) contacting the algae, fungi or botanical biomass with an aqueous liquid to form an aqueous slurry that is essentially organic solvent free, wherein the aqueous liquid comprises about 0.01 wt. % to about 20 wt. %, based on a total weight of the aqueous slurry, of a triblock copolymers of poly(ethylene oxide)/poly(propyleneoxide) defined by the formula (I) or (II)

$$HO(C_2H_4O)_a(C_3H_6O)_b(C_2H_4O)_cOH \qquad (I)$$

or $$HO(C_3H_6O)_b(C_2H_4O)_a(C_3H_6O)_dOH \qquad (II)$$

wherein a and c are independently 3 to 200, and b and d are independently 5 to 100; and
    b) separating the biomass from the aqueous slurry by filtration using a filter comprising a pore size of about 0.1 μm to about 0.5 μm,
wherein the target skin bioactive is a flavonoid or flavonoid derivative, and wherein a total duration of the separating is faster by a factor of at least 2 compared to contacting the algae, fungi or botanical mass with an aqueous liquid that includes water only.

2. The method according to claim 1, wherein the biomass is a flavonoid rich plant, algae or fungi.

3. The method according to claim 1, wherein the flavonoid or flavonoid derivative is selected from compounds comprising the cyclic cores

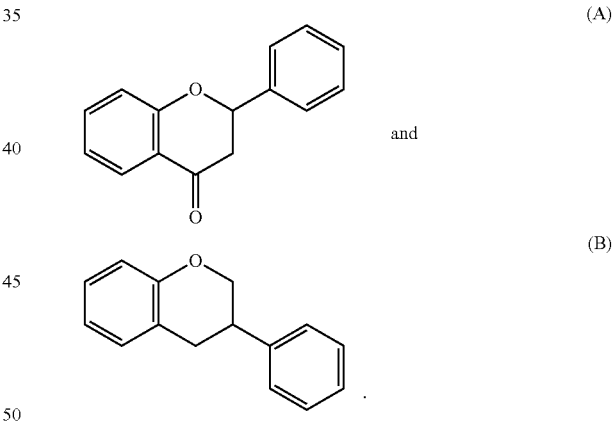

4. The method according to claim 1, wherein the flavonoid or flavonoid derivative is selected from the group consisting of abyssinone I, abyssinone V, afzelechin, ampelopsin, aromadendrin, asebogenin, auriculoside, betagarin, broussin, broussonin C, butin, butrin, (+)-catechin, catechin 7-O-β-xyloside, davidigenin, diffutin, 7,4'-dihydroxyflavan, 2,6-dihydroxyl-4'-methoxydihydro-chalcone, 7,3'-dihydroxyl-4-methoxy-8-methylflavan, 7,4'-dihydroxyl-8-methylfalvan, 6,8-diprenylnaringenin, dracorubin, (−)-epicatechin, ent-epicatechen, epigallo catechin 3-gallate, eriocitrin, eriodictyol, farrerol, fisetinidol, fisetinidol-4-ol, fustin, garbanzol, glabranin, glepidotin β, glycyphyllin, hesperetin, hesperidin, homoeriodictyol, 7-hydroxyflavan, isochamaejasmin, isosakuranetin, isouriaretin, kazinol a, kolaflavanone, liquiretigenin, manniflavanone, 6, methocyaromadendrin 3-O-acetate, 6-methoxytaxifolin, 2'-O-methylodoratol, naringenin, naringin, narirutin, neoastilbin, neoeriocitrin, neohesperidin, odoratol, phloretin, phellamurin, phloretin, phloridzin, pinobanksin, pinocembrin, pinocembrin 7-rhamnosyl-glucoside, piperaduncin β, poncirin, 5'-prenyl, naringenin, pruning, sakuranetin, sanggenon C, sanggenon D, silandrin, silybin, silychristin, sophoranone, strobopinin, taxifolen, taxifolin-3-O-acetate, tephrowatsin, theasinensin A, 2',4',6'-trihydroxyl-3'-formyldihydrochalcone and uvaretin.

5. The method according to claim 1, wherein the biomass is a plant selected from the group consisting of *Cassia alata*, *Argania spinosa* and *Cocoa Callus*.

6. A method of increasing flux during a filtration process of a solid biomass from an aqueous extract, the method comprising:
adding a nonionic surfactant to an aqueous medium comprising the solid biomass, the aqueous medium being essentially organic solvent free; and
extracting the solid biomass, wherein the nonionic surfactant is a triblock copolymers of poly(ethylene oxide)/poly(propyleneoxide) defined by the formula (I) or (II)

$$HO(C_2H_4O)_a(C_3H_6O)_b(C_2H_4O)_cOH \qquad (I)$$

or $$HO(C_3H_6O)_b(C_2H_4O)_a(C_3H_6O)_dOH \qquad (II)$$

wherein a and c are independently 3 to 200, and b and d are independently 5 to 100, and
wherein the aqueous extract comprises at least one of a flavonoid or flavonoid derivative,
wherein the filtration process uses a filter comprising a pore size of about 0.1 μm to about 0.5 μm, and wherein a total duration of the filtration process is faster by a factor of at least 2 compared to extracting the solid biomass with an aqueous liquid that includes water only.

7. A method of increasing the flavonoid extraction from a flavonoid rich plant, the method comprising:
adding a nonionic surfactant to an aqueous medium comprising the flavonoid rich plant, the aqueous medium being essentially organic solvent free; and
extracting the flavonoid rich plant, wherein the nonionic surfactant is a triblock copolymers of poly(ethylene oxide)/poly(propyleneoxide) defined by the formula (I) or (II)

$$HO(C_2H_4O)_a(C_3H_6O)_b(C_2H_4O)_cOH \qquad (I)$$

or $$HO(C_3H_6O)_b(C_2H_4O)_a(C_3H_6O)_dOH \qquad (II)$$

wherein a and c are independently 3 to 200, and b and d are independently 5 to 100,
wherein the extracting comprises a filtration process to separate the plant from the aqueous medium using a filter comprising a pore size of about 0.1 μm to about 0.5 μm, and
wherein a total duration of the extracting is faster by a factor of at least 2 compared to extracting the flavonoid rich plant with an aqueous medium that includes water only.

* * * * *